United States Patent
Debray et al.

(10) Patent No.: US 9,797,778 B2
(45) Date of Patent: Oct. 24, 2017

(54) ACTIVE TERAHERTZ IMAGER

(71) Applicant: CANON KABUSHIKI KAISHA, Tokyo (JP)

(72) Inventors: Alexis Debray, Tokyo (JP); Ryota Sekiguchi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 488 days.

(21) Appl. No.: 14/266,629

(22) Filed: Apr. 30, 2014

(65) Prior Publication Data

US 2014/0326890 A1  Nov. 6, 2014

(30) Foreign Application Priority Data

May 2, 2013  (JP) ................. 2013-096693

(51) Int. Cl.
| | |
|---|---|
| G01J 5/02 | (2006.01) |
| G01J 5/10 | (2006.01) |
| G01J 3/42 | (2006.01) |
| G01N 21/3581 | (2014.01) |
| G01J 5/00 | (2006.01) |

(52) U.S. Cl.
CPC . G01J 5/10 (2013.01); G01J 3/42 (2013.01); G01N 21/3581 (2013.01); *G01J 2005/0077* (2013.01); *G01J 2005/106* (2013.01)

(58) Field of Classification Search
CPC .................. G01N 21/3581; G01N 21/3586
See application file for complete search history.

(56) References Cited

U.S. PATENT DOCUMENTS

| | | | |
|---|---|---|---|
| 7,633,299 B2 * | 12/2009 | Itsuji | G01N 21/3581 324/637 |
| 7,689,070 B2 | 3/2010 | Ouchi | |
| 7,869,070 B2 * | 1/2011 | Sugimoto | H04N 1/0001 348/207.1 |

(Continued)

FOREIGN PATENT DOCUMENTS

| | | |
|---|---|---|
| JP | 2005-020304 A | 1/2005 |
| JP | 2006-300925 A | 11/2006 |
| JP | 2008-275591 A | 11/2008 |

OTHER PUBLICATIONS

"Imaging of broadband terahertz beams using an array of antenna-coupled microbolometers operating at room temperature", Optics Express, Feb. 2013, vol. 21, No. 4, pp. 4817-4825 to Oden at al.*

(Continued)

*Primary Examiner* — Kenneth J Malkowski
(74) *Attorney, Agent, or Firm* — Canon U.S.A. Inc., IP Division

(57) ABSTRACT

An imager for obtaining an image of an object includes a substrate including a plurality of electrical emitting units for emitting electromagnetic waves and a plurality of electrical detecting units for detecting the electromagnetic waves reflected by the object. Each emitting unit includes an electrical emitter, a first antenna, a first metallic reflector, and a first dielectric element between the first antenna and the first metallic reflector. Each detecting unit includes an electrical detector, a second antenna, a second metallic reflector, and a second dielectric element between the second antenna and the second metallic reflector.

19 Claims, 9 Drawing Sheets

(56) References Cited

U.S. PATENT DOCUMENTS 7,884,942 B2    2/2011  Umetsu
2008/0106469 A1* 5/2008  Kikkawa ................. H01L 23/48
                                                    343/700 MS

OTHER PUBLICATIONS

Johnston, et al., "Generation of high-power terahertz pulses in a prism", Optics Letters, Nov. 1, 2002, pp. 1935-1937, vol. 27, No. 21.

Oden, Joanthan, et al.; "Imaging of Broadband Terahertz Beams using an Array of Antenna-Coupled Microbolometers Operating at Room Temperature"; Optics Express, Feb. 25, 2013, pp. 1-10, vol. 21, No. 4.

* cited by examiner

ACTIVE TERAHERTZ IMAGER

BACKGROUND OF THE INVENTION

Field of the Invention

The present invention relates to an active imager for obtaining information of an object by using electromagnetic waves. In particular, the present invention relates to an active imager for obtaining an object image (image information) by using electromagnetic waves in frequency regions from a millimeter wave band to a terahertz wave band (30 GHz to 30 THz) (hereinafter also referred to as THz radiations).

Description of the Related Art

In astronomy, because direct THz radiations to be imaged are extremely weak, the high sensitivity of the sensors used for imaging is obtained by cooling the sensor at cryogenic temperatures. In terrestrial applications, cryogenic cooling being cumbersome for many applications, the sensitivity of the sensors becomes insufficient for direct imaging. As a result, the scene or sample to be imaged must be illuminated by THz radiations while the transmitted or reflected radiations, depending on the configuration of the system, are acquired by the imager. The imager may contain a single sensor or probe scanning a surface or an array of sensors and switches. When this array is part of a camera which utilizes a focal lens, it is known as a focal plane array (FPA).

The sensitivity of terahertz sensors operating at room temperature is too low to achieve direct imaging in most applications. The power per unit frequency of radiations emitted by a blackbody at 300 K, 1 THz, for a 1 millimeter square surface and 1 steradian is roughly $10^{-19}$ W/Hz. Supposing the sensor being filtered with a frequency band of 100 GHz, the energy reaching one pixel is roughly 10 pW. Today's best sensors in the THz range and operating at room temperature possess a noise equivalent power (NEP) not better than 4 pW/√Hz. Using a scanning frequency band of 1 kHz, they achieve a signal-to-noise ratio of 1 when the input power is 126 pW. When measuring a blackbody at 1 THz with the above conditions, the signal-to-noise ratio is $8 \times 10^{-2}$. This signal-to-noise ratio is too low to extract any signal from the background noise in most applications. In order to increase the signal-to-noise ratio, it is therefore necessary to illuminate the scene or sample to be imaged with terahertz radiations. In other words, it is necessary to achieve active imaging. This situation is similar to optical photography, in which the scene is either illuminated by the light of the sun or an artificial light, for example a flash, or a combination of both.

U.S. Pat. No. 7,884,942 of Tomoyuki Umetsu discloses a probe apparatus and terahertz spectrometer. The probe consists of two photoconducting pairs of electrodes integrated on a substrate and two lenses on the opposite side of the substrate, each one facing, through the substrate, one of the two pairs of electrodes. A laser beam is focused on each pair of electrodes. One pair of electrodes is used for emission while the other one is used for detection. As the laser light impinges on the emitting pair of electrodes, THz radiations are emitted in the substrate and propagate into the lens. Thanks to the geometry of the lens, these radiations are focused on a particular position on a sample facing the lens. The THz radiations reflected by the sample are then collimated by the lens facing the detecting pair of electrodes and propagate through the substrate until the detecting pair of electrodes. When the laser beam impinges on the detecting pair of electrodes, the resistivity between the electrodes is lowered and an electric signal can be recorded by the electrodes. Due to a particular angle of the axis of both lenses, the position on the sample on which the emitted THz radiations from the emitting lens impinges corresponds to the position on the sample by which the reflected THz radiations are collimated by the detecting lens. The probe can be scanned along a surface in order to produce an image. However, mechanically scanning a variety of positions requires a large amount of time and cannot lead to high frame rates. Alternatively, an array of such pair of emitting and detecting electrodes and lenses is provided by the application in order to produce an image without resorting to a mechanical scanning and therefore in order to achieve a higher frame rate than in the case of mechanical scanning. In this application, in order to condensate the radiations propagating through the substrate, one lens is needed for each pair of electrodes. In order to be effective, the diameter of the lens must be larger than several wavelength of radiation collimated by the lens according to the calculation of the Airy disk. For example, if radiations are emitted at 1 THz, then the wavelength of the radiations is 300 μm, and the diameter of the lens must be more than 1 mm in order for the lens to be effective as a focusing element. As two lenses are needed for each pair of emitting and detecting electrodes, the distance between two sensing elements, or in other words the distance between two consecutive pixels, is also several wavelengths. As a result, the lateral resolution of this imager is limited to several times the imaging wavelengths in order to be efficient.

M. B. Johnson et al. (M. B., Johnston, et al. Generation of high-power terahertz pulses in a prism. s.l.: Optics Letters, 2002. 27(21)) have reported on the generation of THz pulses in a prism. In this reference, THz radiations are generated applying a laser pulse on an InAs epilayer placed on a bulk GaAs prism and the mechanism which produces the THz radiations is that of the photo-Dember effect. The presence of the prism is responsible for a particular orientation of the dipole generated by the laser in the InAs epilayer, leading to a high power for the terahertz radiations. Depending on the applications, collimation of the THz radiations by a focusing element, such as a lens, may not be necessary, even if the authors state that collection optics leads to higher powers of the THz radiations. Again, one limitation of this reference is the size of the optional collection optics which diameter should be more than several wavelengths of the emitted THz radiations. Another limitation is the width of the GaAs prism which is reported by the authors to be more than 700 μm whereas the wavelength of the emitted radiations is roughly 300 μm. Finally, the geometrical arrangement of the system is another of its limitations. A laser beam must be directed at 45° on the same surface that emits the THz radiations. As a consequence, the emitting surface of the system must by cleared off and the system cannot be used for imaging samples which are in close distance to it or in contact to it.

U.S. Pat. No. 7,689,070 of Toshihiko Ouchi discloses on a high frequency electrical signal control device and sensing system. In this reference, a first laser beam impinges on an emitting photoconductive electrode, and a second laser beam impinges on a detecting photoconductive electrode. The emitted THz radiations and the THz radiations used for detection are transmitted from the electrodes to a single antenna using electrical connections or waveguides. The emitted and detected THz radiations propagate perpendicularly to the surface of the substrate and not in the substrate. As a result, no focusing element such as a lens is needed. However, because the emitted and detected radiations use the same antenna, they need to be separated in the circuitry.

This operation can be performed by a delay line, and especially a mechanical delay line. As a result, the operation of this delay line prevents the realization of instant imaging.

The disclosures of the previous references are capable of providing active imaging in the THz range. However, some are limited in the lateral resolution which can be obtained. Some others are limited to samples or scenes which are far away from the sample, or they are limited to slow response because of the presence of delay lines.

SUMMARY OF THE INVENTION

The present application discloses an active imager in the THz range which lateral resolution is in the order of the wavelength being imaged. Moreover, this imager should be able to be used in close distance to the sample being imaged or even in contact with the sample. Finally, it should be possible to simultaneously achieve the emission and detection of radiations.

In one aspect of the present invention, an imager for obtaining an image of an object includes a substrate including a plurality of electrical emitting units for emitting electromagnetic waves and a plurality of electrical detecting units for detecting the electromagnetic waves reflected by the object. Each emitting unit includes an electrical emitter, a first antenna, a first metallic reflector, and a first dielectric element between the first antenna and the first metallic reflector, and each detecting unit includes an electrical detector, a second antenna, a second metallic reflector, and a second dielectric element between the second antenna and the second metallic reflector.

Further features of the present invention will become apparent from the following description of exemplary embodiments with reference to the attached drawings.

DESCRIPTION OF THE EMBODIMENTS

Embodiments of the present invention will be described below with reference to the accompanying drawings. In the Embodiments, a plurality of electrical emitting units and a plurality of electrical detecting units are arranged on substantially the same surface, and a distance between two consecutive detectors is short. For example, the distance is less than twice the imaging wavelength (a wavelength of the electromagnetic waves used for imaging). This arrangement enables the imager to detect the electromagnetic waves with high resolution. In order to emit the electromagnetic waves effectively and to detect the electromagnetic waves effectively, metallic reflectors facing antennas have important roles in the emitting units and the detecting units. The emitting units and detecting units may be arranged in several manners. As described in following embodiments, each emitting unit may correspond to each detecting unit with a one to one relation. Emitting units may correspond to a single detecting unit. A single emitting unit may correspond to detecting units.

Figure 1:
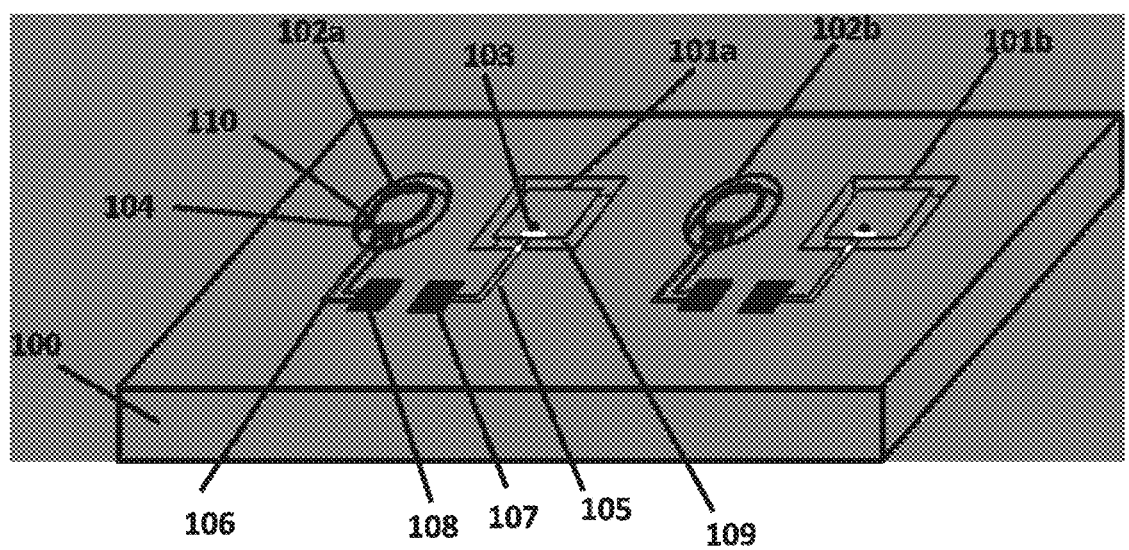
FIG. 1 is a perspective view of the device according to a first embodiment of the invention.
Figure 7:
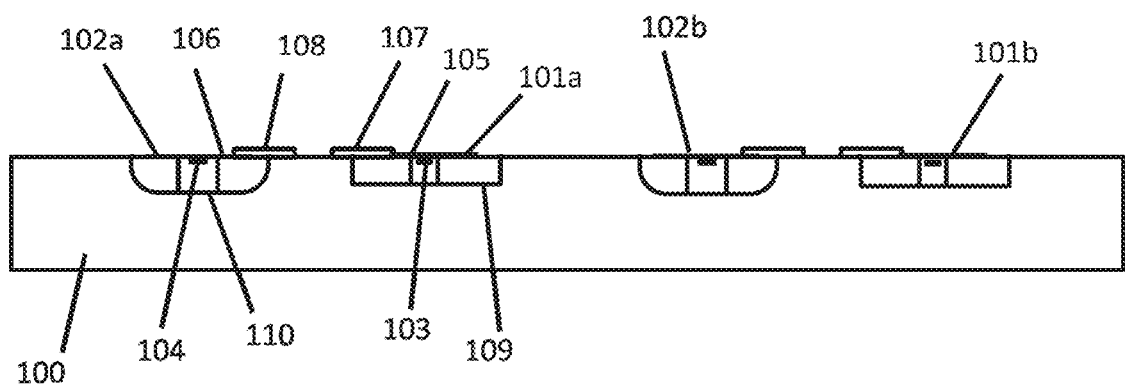
FIG. 7 is a cross-sectional view of the device according to the first embodiment of the invention.

An imager (device) according to a first embodiment of the present invention is now described. A perspective view of the device is shown in FIG. 1. A cross-sectional view of the device is shown in FIG. 7. The device comprises a substrate 100. For example, the substrate consists of a semiconductor wafer which can be made of silicon, GaAs, InP or any other semiconductor material of interest. The substrate integrates a plurality of emission antennas 101a, 101b . . . (collectively denoted as 101) for emission and a plurality of detection antennas 102a, 102b . . . (collectively denoted as 102) for detection. For each emission antenna, an electrical emitter 103 connects to the emission antenna 101 and to an integrated electronic circuit 107 via electric lines 105. The electrical emitter 103 generates electromagnetic waves which are radiated by the emission antenna 101. An electrical detector 104 converts the electromagnetic waves in the detection antenna 102 into an electrical signal which is transmitted by electric lines 106 and processed by an integrated electronic circuit 108. In this specification, electrical emitter or electrical detector means an element which can emit or detect electromagnetic waves not by irradiating the element with exciting light, but by electric control. That is to say, electrical emitter or electrical detector is a current injection type element.

Although various electrical detectors 104 can be envisioned in order to process the signal originating detection antennas, rectifying elements are of particular interest because of the simplicity of their fabrication and because they can operate at frequencies above 1 THz. Among these rectifying elements, the Schottky barrier diode has been investigated for decades in the THz range and can be operated at room temperature. One example of a Schottky barrier diode is as follows. Two metal layers constituting a $\lambda/2$ dipole antenna come into contact with a low carrier concentration semiconductor and a high carrier concentration semiconductor on the nonconductive substrate, respectively. The two metal layers are made of a schottky metal and an ohmic metal, respectively. The Schottky barrier diode is made up of the schottky metal, the low carrier concentration semiconductor, the high carrier concentration semiconductor, and the ohmic metal. Hence, the two metal layers form the $\lambda/2$ dipole antenna, and also serve as an electrode of the Schottky barrier diode element. A length direction of the metal layer is a resonant direction of the electromagnetic wave. $\lambda$ is a wavelength of the electromagnetic wave to be detected, which is not in a vacuum but is an effective wavelength multiplied by a wavelength compression ratio depending on a substrate. The details of which are provided in US2011/0248724, all of which are incorporated herein by reference in their entirety.

As the electrical detectors 104, a thermal detecting device or a quantum detecting device can be used. A thermal detecting device may be a microbolometer that uses material such as a-Si, VOx, or the like, a pyroelectric element that uses material such as LiTaO3, TGS, or the like, and a Golay cell, or the like. Such a thermal detecting device is a device that can convert electromagnetic wave energy into heat energy, and detect changes in thermoelectric power. A quantum detecting device may be an intrinsic semiconductor device that uses a semiconductor having no accepter or donor doping (MCT, photoconductive device, etc.) or an extrinsic semiconductor device that uses a semiconductor to which an acceptor or donor has been added, or doped. Such a quantum detecting device is a device that captures the electromagnetic waves as photons, and detects the photovoltaic power or resistance changes from the semiconductor having a smaller band gap. As the electrical emitter, various electrical emitters (differential negative resistance element, etc.) can be envisioned in order to generate the radiations to illuminate the sample or the scene to be imaged. Among these differential negative resistance elements, the resonant tunneling diode is one example. Some devices have been reported to operate at frequencies at 1 THz at room temperature. The power source supplies current required for driving the negative differential resistance element and controls a static voltage of an operating point. The operating point is typically selected from a negative resistance region. The electrical emitting unit, for example, includes an RTD and a patch antenna formed of metal patterning. An RTD includes, for example, a multiple quantum well structure of InGaAs/InAlAs and InGaAs/AlAs and electrical contact layers of n-InGaAs which are formed on an InP substrate. For example, a triple-barrier structure is used as the multiple quantum well structure. More specifically, a semiconductor multi-layer structure of AlAs/InGaAs/InAlAs/InGaAs/AlAs is used. Of those layers, the InGaAs layer is a well layer, and the lattice-matched InAlAs layer and the lattice-mismatched AlAs layer are barrier layers. Those layers are in an undoped state without intentional carrier doping. Such a device can be manufactured by the following manufacturing method. First, the following layers are epitaxially grown on the InP substrate by molecular beam epitaxy (MBE), metalorganic vapor phase epitaxy (MOVPE), or the like. Specifically, an n-InP/n-InGaAs layer and an InGaAs/InAlAs layer are epitaxially grown in this order to form the resonant tunneling diode. In the case where an n-type conductive substrate is selected as the InP substrate, the resonant tunneling diode may be epitaxially grown from an n-InGaAs layer. Next, the resonant tunneling diode is etched into a circular mesa shape. Then, the resonant tunneling diode is further etched into an arc mesa shape. For etching, dry etching using electron beam (EB) lithography and inductive coupling plasma (ICP) is used. Photolithography may be used instead. Subsequently, a ground metal is formed on the etched surface by lift-off. A passivation film may be formed to protect the side wall of the resonant tunneling diode. Then, an insulator is embedded, and Ti/Pd/Au patterns are formed by lift-off. Finally, a bismuth pattern is formed by lift-off in a region to be the resistor, and the Ti/Pd/Au pattern is connected to the ground metal via the formed bismuth through-hole. The details of which are provided in US2012/0068778, all of which are incorporated herein by reference in their entirety. As the electrical emitter 103, an element which generates electromagnetic waves (THz radiations) by intersubband transition of carriers can be used. An example of the element is a Quantum Cascade Laser (QCL).

In order to limit the emitting antenna 101 to emit radiations into the substrate 100, a metallic ground plane 109 is provided between the antenna 101 and the bulk of the substrate 100. Also, in order to limit the radiations impinging on the substrate 100 to penetrate this last, a metallic reflector 110 is provided at the bottom of the recess. The metallic ground plane and the metallic reflector can be fabricated by metal deposition, lithography and etching, or by metal deposition and lift-off. In order to reduce the fabrication cost of the device, it is of interest that both the metallic ground plane and the metallic reflector be processed during the same steps. As a result, the metal element constituting the metallic ground plane is the same as the one constituting the metallic reflector. Also, during the fabrication process, the metallic layer forming the metallic ground plane is the same as the one forming the metallic reflector, and they are both etched during the same steps, only differing by their planar shape which is, for example, defined by a photolithographic mask.

In order to mechanically support the emission and detection antennas 101, 102, dielectric elements are provided between the emission antenna and the ground plane 109 as well as the detection antenna and the reflector 110. In order to obtain a good interaction between the waves propagating in the medium surrounding the substrate 100 and those propagating in the dielectric elements, it is necessary that the relative permittivity of the dielectric be close to that of the material surrounding the substrate. For example, if the substrate is surrounded by air, it is necessary that the relative permittivity of the dielectric elements is close to that of air, that is close to 1. An interesting material for the dielectric elements is for example BCB (benzocyclobutene) which relative permittivity is close to 2.4 in the THz range. In order to simplify the fabrication of the device, and therefore reduce its fabrication cost, it is of interest to process the dielectric elements of the emitters and the detectors during the same fabrication steps. As a result, the material constituting the dielectric elements of the emitters is the same as the dielectric element of the receptors and both are processed using the same steps, for example the same deposition step, the same baking steps and patterning steps. Similarly, in order to simplify the fabrication of the device and therefore its cost, it is of interest to process the emission antennas, the detection antennas and the electrical connections of both devices during the same fabrication steps because they are all made of metal and lay on top of the substrate. As a result, the emission antennas, the detection antennas and the electrical connections of both devices are made of the same metal.

Figure 2:
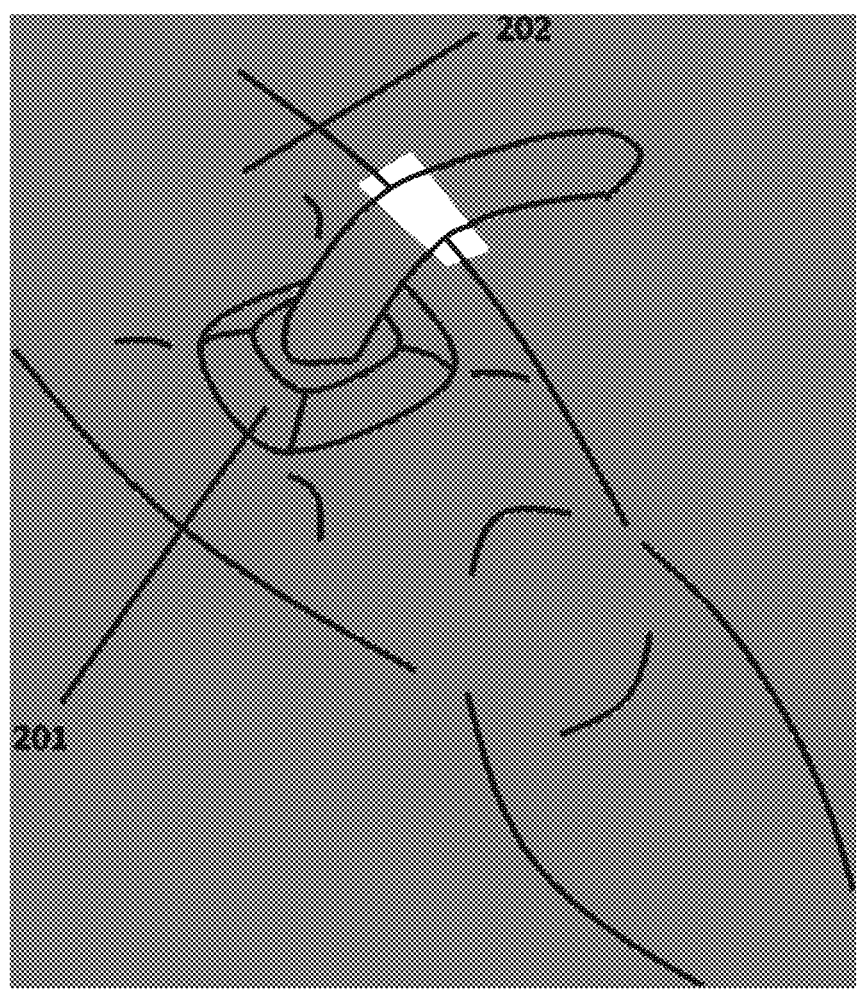
FIG. 2 shows the device according to the first embodiment integrated into a probe and used as a contact imager in order to image the skin of a human thigh.

FIG. 2 shows the device according to the first embodiment integrated into a probe 201 and used as a contact imager in order to image the skin of a human thigh 202. The device is integrated into a probe and used such that the array of emitters and detectors face the sample to be imaged. Particularly, the sample can be a living tissue, as for example the skin of a human thigh, or any tissue which can be made accessible thanks to surgery. Because THz radiations are able to distinguish between cancer tissue and normal tissue, this probe can be used to investigate the presence of cancer in a patient. Moreover, the probe can be made into contact with the sample. In this case, THz radiations are emitted by the array of emitters of the device and partially reflected by the sample. These reflected radiations are then detected by the array of detectors of the device. In this contact configuration, a thin element in form of a window is likely to be placed between the sample and the device in order to protect this last from contaminations. It is of interest to have this window being transparent to THz radiations. It is also of interest to have the dielectric permittivity of the material forming this window to be as close as possible to the dielectric permittivity of the material forming the dielectric element between the antennas and the substrate in order to avoid any impedance matching at the interface between the two. In this contact configuration, it is also of interest to have the dielectric permittivity of these materials being different from that of skin in order to provide a maximum reflection coefficient at the interface between the window and the skin, and therefore a maximum energy reflected to the detector, providing a large signal to noise ratio. Also, in this contact configuration, the lateral spatial resolution of the imager is the distance between two consecutive detectors and is not dependent on optical elements.

Besides this contact configuration, it can be of interest to have the imager out of contact with the sample, for example when the surface of the sample to image is delicate as it is the case with living tissue revealed by surgery. If the imager is at close distance from the sample to image but not in contact with its surface, the lateral spatial resolution and quality of the image may be reduced as the imager is farther from the contact position.

Figure 3:
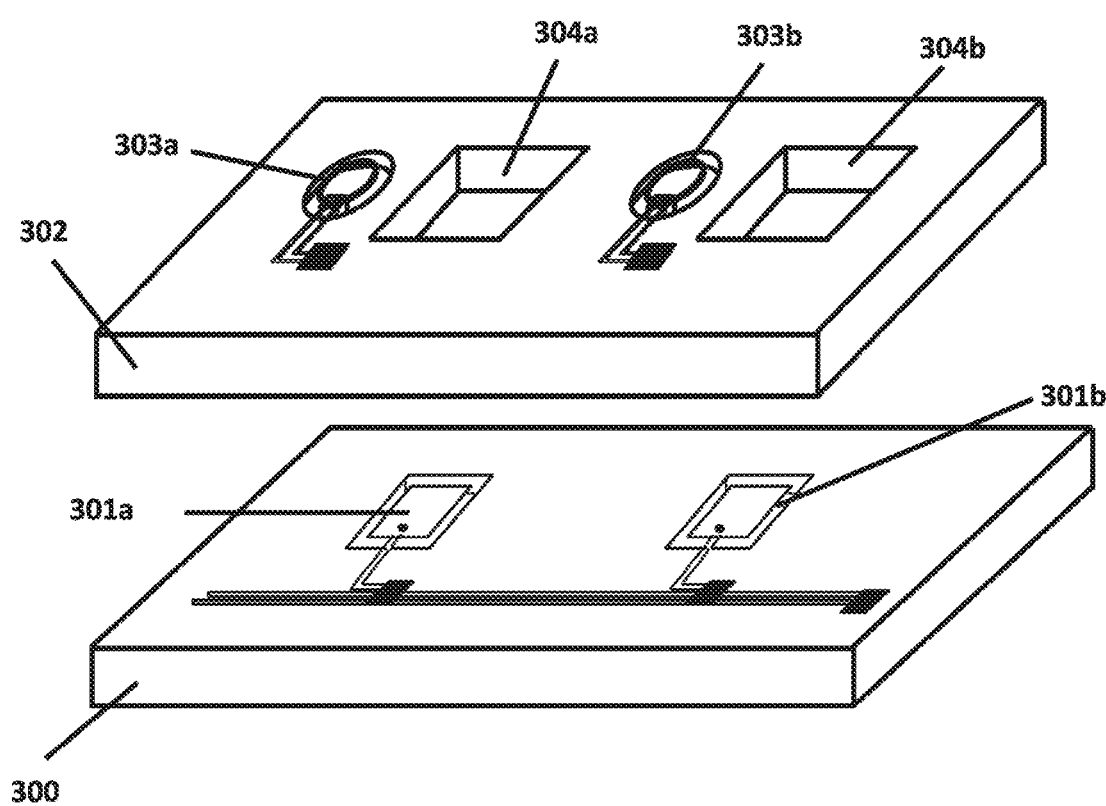
FIG. 3 is a perspective view of the device before assembly according to a second embodiment of the invention.
Figure 4:
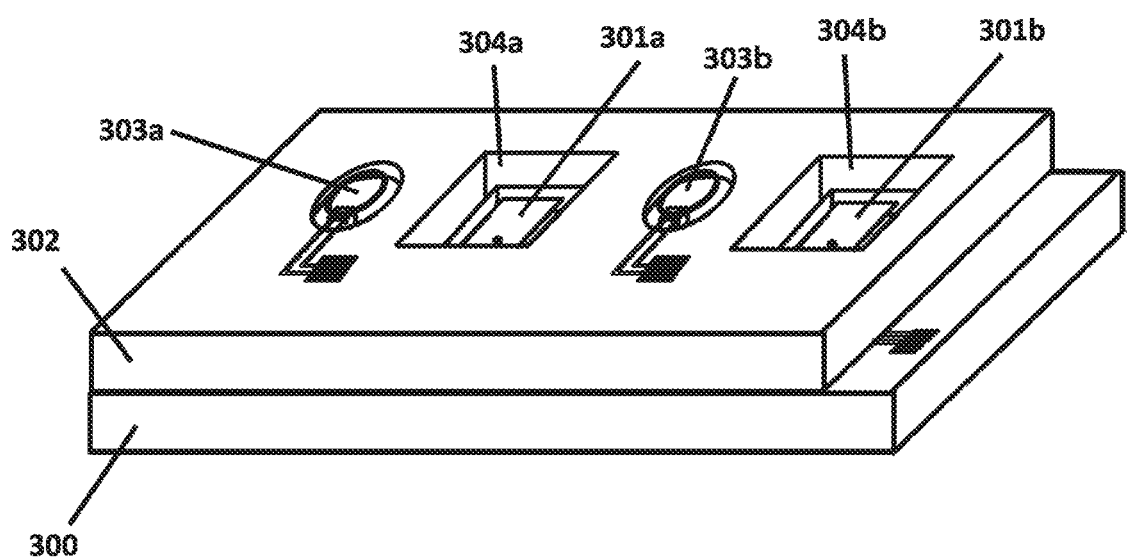
FIG. 4 is a perspective view of the device after assembly according to the second embodiment of the invention.
Figure 8:
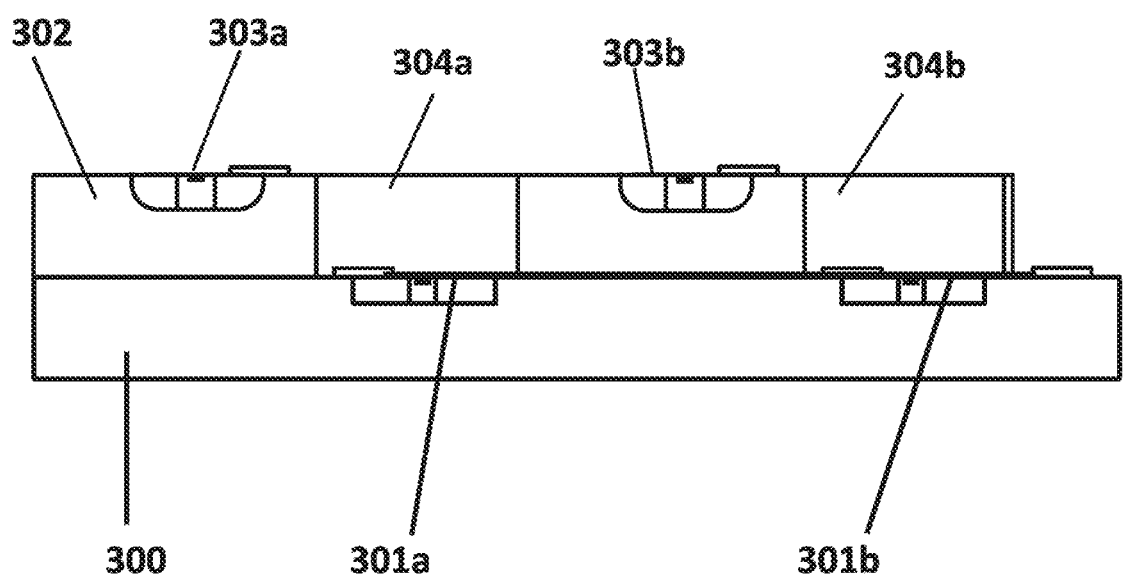
FIG. 8 is a cross-sectional view of the device according to the second embodiment of the invention.

An imager (device) according to a Second embodiment of the present invention is now described. In order to achieve high performances for both the electrical emitters and the electrical detectors, it may be necessary to utilize different semiconductors for their fabrication. Although the deposition of dissimilar semiconductors on a single substrate is possible in some cases using, for example, local epitaxy, some combinations of dissimilar semiconductors on a single substrate are still difficult to achieve or are prohibitive from an economical point of view. As a result, a more general solution enabling the use of dissimilar semiconductors for the emitters and the detectors is of interest. This is the subject of the second embodiment. FIG. 3 illustrates the device before assembly. FIG. 4 illustrates the device after assembly. FIG. 8 is a cross-sectional view of the device.

In the second embodiment, a first substrate (emitter substrate) 300 which contains a plurality of emitting units 301a, 301b . . . (collectively denoted as 301) is provided. The plurality of emitting units is similar to the one described in the first embodiment. Each emitting unit includes at least an emitter, an electronic circuitry, electric lines connecting the emitter to the electronic circuitry, an antenna, a ground plane, and a dielectric element between the ground plane and the antenna and supporting the antenna. A second substrate (detector substrate) 302 which contains a plurality of detecting units 303a, 303b . . . (collectively denoted as 303) is provided. The plurality of detecting units is similar to those described in the first embodiment. Each detecting unit includes at least a detector, an electronic circuitry, an antenna, electric lines connecting the electronic circuitry to the antenna, a reflector, and a dielectric element between the reflector and the antenna and supporting the antenna. The detector substrate 302 is also provided with a plurality of channels 304a, 304b . . . (collectively denoted as 304) through all its thickness. The emitter substrate and the detector substrate are assembled together. They can be assembled by wafer bonding, for example direct bonding, adhesive bonding, surface activated bonding or any other known wafer bonding technique. Or they can be assembled by some external pressure pressing each other against one another.

The design of the second embodiment is such that the plurality of channels 304 of the detecting substrate aligns with the plurality of emitting units 301 of the emitter substrate 300 when both substrates are assembled together. As a result, the radiations emitted by the emitters propagate in the space in front of the detector substrate through the plurality of channels 304. In order to prevent the radiations emitted by the plurality of emitters to propagate in the detector substrate 302, and therefore to directly interfere with the plurality of detectors, it might be of interest to cover the walls of the channel with a metallic layer. In order to prevent an impedance mismatch between the channel 304 and the emitting antenna, the dielectric permittivity of the material placed between the emitting antenna and the substrate should be close to that of the material filling the material. Moreover, when the device is used as a contact imager, it is of interest that the dielectric permittivity of the two is different from that of the material to be imaged in order to provide a large energy reflected to the detecting units 303.

In order to improve the propagation of the radiations from the plurality of emitting units through the channel, it is of interest to shape the channel such that its cross sectional area is smaller close to the emitter and larger at the opening. If the detector substrate 302 is made of silicon, the channel can be etched by anisotropic etchants like TMAH (Tetramethylammonium hydroxide) or KOH. Moreover, using the microloading effects, the channel can be etched in order to produce round shapes. Finally, a combination of various etching techniques can lead to various shapes for the channel. The aspect ratio of the channel depends on the size of the antenna of the emitting units 301 and the thickness of the detector substrate 302. It might happen that for certain designs of antenna or certain frequencies, the aspect ratio of the channel is too high for a proper propagation of the radiations emitted by the plurality of emitting units. In order to overcome this problem, it is possible to thin the detector substrate prior to assembly. For example, the detector substrate can be thinned to a thickness as low as 50 μm or 100 μm.

Depending on the application, it might be of interest to replace the position of the plurality of detecting units 303 with that of the plurality of emitting units 301 and vice versa. As a result, the second embodiment also describes all the inventions in which the position of the plurality of detecting units is exchanged with that of the plurality of emitting units and vice versa.

Figure 5:
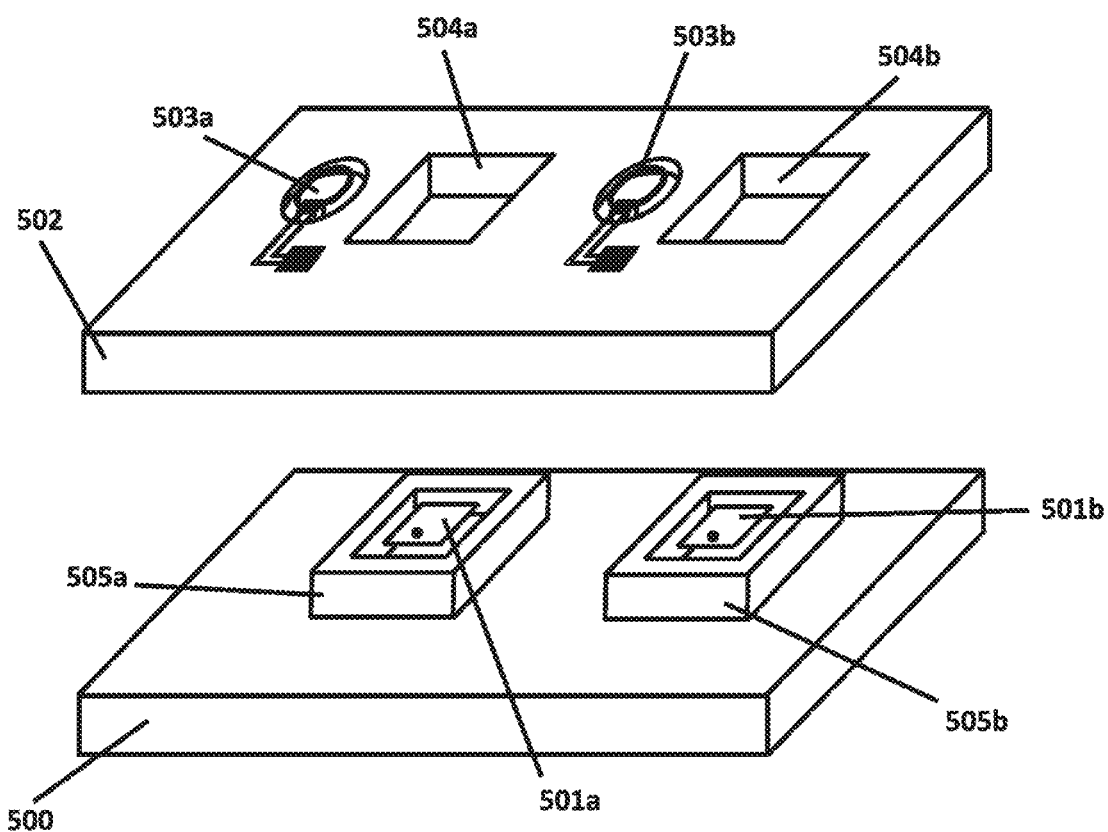
FIG. 5 is a perspective view of the device before assembly according to a third embodiment of the invention.
Figure 6:
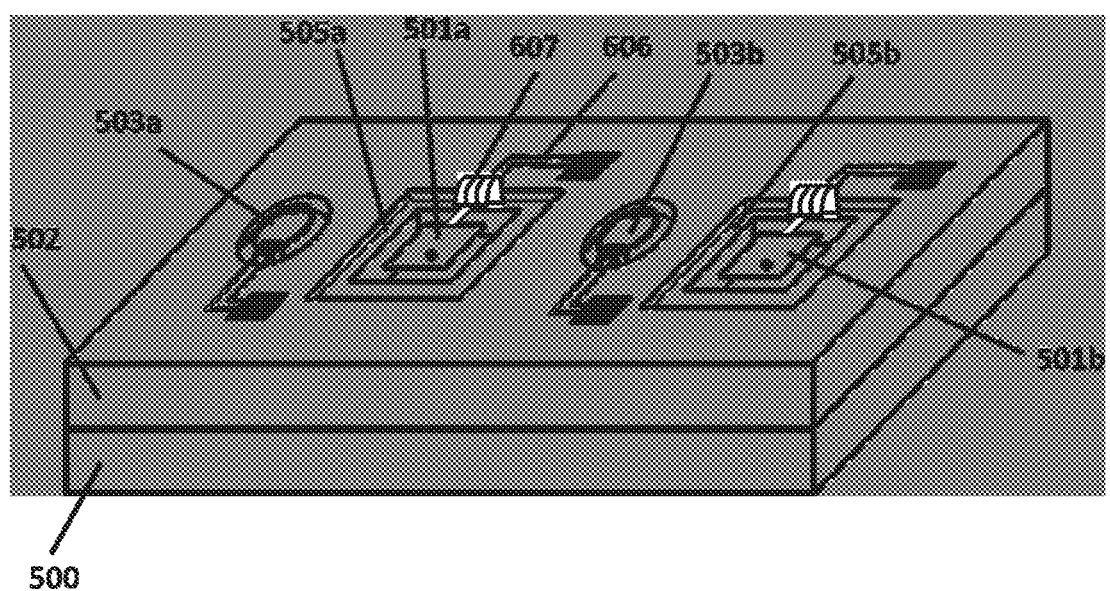
FIG. 6 is a perspective view of the device after assembly according to the third embodiment of the invention.
Figure 9:
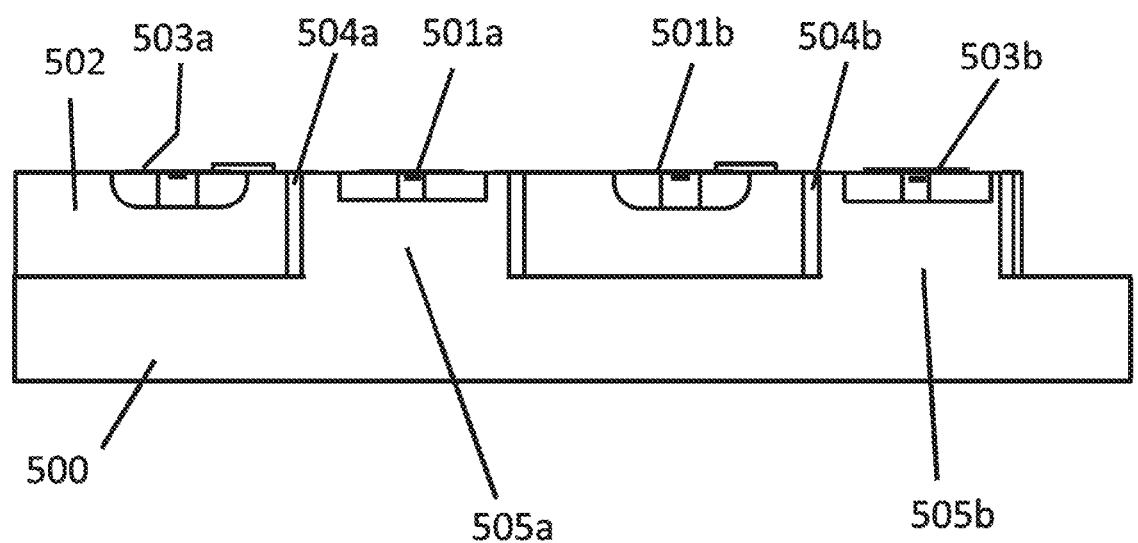
FIG. 9 is a cross-sectional view of the device according to the third embodiment of the invention.

An imager (device) according to a Third embodiment of the present invention is now described. FIG. 5 illustrates the device before assembly. FIG. 6 illustrates the device after assembly. FIG. 9 is a cross-sectional view of the device.

A first substrate (detector substrate) 502 with a plurality of detecting units 503a, 503b . . . (collectively denoted as 503) and a plurality of channels 504a, 504b . . . (collectively denoted as 504) is provided. The substrate 502 is similar to the substrate 302 presented in the second embodiment. A second substrate (emitter substrate) 500 is provided. The second substrate contains a plurality of pillars 505a, 505b . . . (collectively denoted as 505). On the top of each pillar an emitting unit 501a, 501b . . . (collectively denoted as 501), similar to the emitting unit presented in the first embodiment, is provided. The shape of the pillars is such that they fit into the channels 504a, 504b . . . (collectively denoted as 504) of the detector substrate 502. In case the emitter substrate is made of silicon, the pillar can be formed, for example, by photolithography and deep reactive ion etching. In this case, the walls of the pillars can be made vertical and fit into the channels, which walls that are also vertical and formed also by photolithography and deep reactive ion etching. Differently, it might be interesting to have the walls of the pillar inclined in order to allow the fabrication of electrical lines on the walls of the pillars. Inclined walls can be achieved by photolithography and anisotropic etching such as TMAH or KOH. Fabrication of electrical lines on the inclined walls can be achieved by metal deposition and photolithography by spray coating and maskless photolithography. As a result of these inclined walls, the emitting units resting on the pillars can be easily connected to the outside walls. In case the electrical connections 606 of the emitting units are not fabricated on the walls of the pillars 505a, 505b . . . , they must rest partly on the pillars and partly on the top surface of the detector substrate 502. Due to the necessity to embed the pillars in the channels, there is necessarily a gap between the top surface of the pillars and the top surface of the detector substrate. In order to have continuity in the electrical connections 606, it is of interest to provide an insulating element 607 to cover the gap between the top surface of the pillars and the top surface of the detector substrate. This insulating element 607 can be provided by standard spin coating deposition or spray coating deposition followed by a direct photolithographic patterning if the material is itself photosensitive, or by a photolithographic patterning using a photo-resistive mask and a chemical or physical etching, for example using an oxygen plasma etching.

Alternatively, the insulating element 607 can be directly deposited by micro-dispensing. The electrical connections 606 are then fabricated by a standard metal deposition and etching by photolithography techniques for example. Depending on the application, it might be of interest to replace the position of the plurality of detecting units 503 with that of the plurality of emitting units 501 and vice versa. As a result, the third embodiment also describes all the inventions in which the position of the plurality of detecting units is exchanged with that of the plurality of emitting units and vice versa.

Because the device provided by the Embodiments of this invention provides simultaneously emitters and detectors in the THz range, it is suitable for active imaging in this frequency range. Because the emitters and the detectors are solely electrical devices, it is possible to prevent their corresponding radiations from propagating into the substrate. This can be achieved, for example, by incorporating metallic reflectors between their radiating elements and the substrate. As a result, the use of collimating optics, such as a lens, is not needed. The size of the emitters and the detectors is basically limited by that of the antenna, which can be made the same size as the wavelength of the radiation to be imaged, or even smaller. Therefore, the distance between two consecutive detectors can be made much smaller than in the case when lenses are used. As a result, the lateral resolution of the imager is greatly improved compared to the case when lenses are used. Another benefit of the Embodiments of this invention is that there is no need to use a laser beam between the device and the sample or scene. As a result, the Embodiments provide an imager which can be used at a close distance from the sample, or even in contact to the sample.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-096693, filed May 2, 2013, which is hereby incorporated by reference herein in its entirety.

What is claimed is:

1. An imager for obtaining an image of an object, comprising:
   a substrate including a plurality of electrical emitting units configured to emit electromagnetic waves and a plurality of electrical detecting units configured to detect the electromagnetic waves reflected by the object,
   wherein each emitting unit includes an emitter, a first antenna connected to the emitter, a first reflector provided between the first antenna and the substrate and facing the first antenna, and a first dielectric element provided between the first antenna and the first reflector, and
   wherein each detecting unit includes a detector, a second antenna connected to the detector, a second reflector provided between the second antenna and the substrate and facing the second antenna, and a second dielectric element provided between the second antenna and the second reflector.

2. The imager according to claim 1, wherein a distance between two consecutive detectors is less than twice the wavelength of the electromagnetic waves.

3. The imager according to claim 1, wherein the electromagnetic waves include THz radiations.

4. The imager according to claim 1, wherein each of the first and second reflectors are made of the same material.

5. The imager according to claim 1, wherein the first and second dielectric elements are made of the same material.

6. The imager according to claim 1, wherein the first and second antennas are made of the same material.

7. The imager according to claim 1, wherein each emitter includes a differential negative resistance element.

8. The imager according to claim 1, wherein each emitter includes a resonant tunneling diode.

9. The imager according to claim 1, wherein each emitter includes a Quantum Cascade Laser.

10. The imager according to claim 1, wherein each detector includes a rectifier.

11. The imager according to claim 10, wherein the rectifier is a Schottky barrier diode.

12. The imager according to claim 11, wherein the second antenna includes a Schottky electrode of the Schottky barrier diode and an ohmic electrode of the Schottky barrier diode.

13. The imager according to claim 1, wherein the emitter is provided between the first antenna and the first reflector.

14. The imager according to claim 1, wherein the electromagnetic waves from each of the plurality of emitting units is radiated over the substrate.

15. The imager according to claim 1, further comprising:
   a power source configured to supply a voltage to the emitter; and
   a circuit connected to the detector and configured to process a signal from the detector.

16. The imager according to claim 1, wherein the first antenna and the first reflector constitute a patch antenna where the electromagnetic waves resonates.

17. An imager for obtaining an image of an object, comprising:
   a substrate including a plurality of emitting units and a plurality of detecting units,
   wherein each emitting unit includes an emitter, a first metallic element connected to the emitter, a first dielectric element provided in the substrate and supporting the first metallic element, and a first reflector facing the first metallic element via the first dielectric element, and
   wherein each detecting unit includes a detector, a second metallic element connected to the detector, a second dielectric element provided in the substrate and supporting the second metallic element, and a second reflector facing the second metallic element via the second dielectric element.

18. The imager according to claim 17, wherein the emitter is a negative resistance element and is disposed between the first metallic element and the first reflector.

19. The imager according to claim 17, wherein the detector is a Schottky barrier diode, and
   wherein the second metallic element includes a Schottky electrode of the Schottky barrier diode and an ohmic electrode of the Schottky barrier diode.

\* \* \* \* \*